(12) United States Patent
Alexandersen (10) Patent No.: US 6,468,245 B2
(45) Date of Patent: *Oct. 22, 2002

(54) IRRIGATION DEVICE

(75) Inventor: Morten Bay Alexandersen, Aalsgaarde (DK)

(73) Assignee: Colorplast A/S, Humlebaek (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,627

(22) PCT Filed: Nov. 27, 1997

(86) PCT No.: PCT/DK97/00544

§ 371 (c)(1),
(2), (4) Date: May 26, 1999

(87) PCT Pub. No.: WO98/23312

PCT Pub. Date: Jun. 4, 1998

(65) Prior Publication Data

US 2002/0019613 A1 Feb. 14, 2002

(30) Foreign Application Priority Data

Nov. 27, 1996 (DK) .............................. 1356/96

(51) Int. Cl.$^7$ .............................................. A61M 29/00
(52) U.S. Cl. ..................................................... 604/105
(58) Field of Search ................................ 604/279, 275, 604/265, 264, 93.01, 257, 263, 95.01, 95.02, 96.01, 104, 105, 106, 523

(56) References Cited

U.S. PATENT DOCUMENTS

| | | | |
|---|---|---|---|
| 3,459,175 A | 8/1969 | Miller | 128/2 |
| 3,766,920 A | 10/1973 | Greene | 128/246 |
| 3,815,608 A * | 6/1974 | Spinosa et al. | 128/349 |
| 3,889,676 A * | 6/1975 | Greene | 128/246 |
| 3,990,448 A | 11/1976 | Mather et al. | 128/239 |
| 4,241,735 A * | 12/1980 | Chernov | 128/344 |
| 4,386,607 A * | 6/1983 | Miller | 604/37 |
| 5,653,690 A * | 8/1997 | Booth et al. | 604/96 |
| 5,674,287 A * | 10/1997 | Slepian et al. | 623/11 |
| 5,882,345 A * | 3/1999 | Yoon | 604/264 |
| 5,947,977 A * | 9/1999 | Slepian et al. | 606/108 |

FOREIGN PATENT DOCUMENTS

| | | |
|---|---|---|
| EP | 0 109 897 | 5/1984 |
| GB | 2 224 212 | 5/1990 |
| WO | WO95/28138 | 10/1995 |

* cited by examiner

Primary Examiner—Anhtuan T. Nguyen
Assistant Examiner—Ann Y Lam
(74) Attorney, Agent, or Firm—Jacobson Holman, PLLC (57) ABSTRACT

The present invention relates to a device (1) for irrigation of externally debouching, natural or artificial body canals of animals or human beings. The device comprises a catheter (2), and optionally a container (3) designed for containing irrigation medium (4) and a tube member (5) connecting the catheter (2) with the container (3). The catheter is provided with a fixation member (6) for fixation of the catheter inside the body canal and for providing a liquid tight seal between the catheter (2) and the body canal, which fixation member (6) automatically fixates and seals around the catheter (2) when placed in the body canal. The invention further relates to a method of producing the device. Finally, the invention relates to the use of the device (1) for performing irrigation on a person.

33 Claims, 10 Drawing Sheets

IRRIGATION DEVICE

BACKGROUND OF THE INVENTION

1. Field of the Invention

The present invention relates to a device for irrigation of externally debouching, natural or artificial body canals of animals or human beings, to a method of producing such a device, and to the use of such a device for performing an irrigation of externally debouching, natural or artificial body canals of animals or human beings. The device is especially suitable as a disposable "ready to use" kit for trans-anal irrigation.

2. Description of the Prior Art

Continence can be defined as the ability to control defaecation, to be able to distinguish flatus from loose respectively formed faeces and to be able to maintain continence even during sleep without the use of external aids.

British studies have shown the prevalence of faecal incontinence in the adult population to be 0.5% approximately and the prevalence among women over 65 years of age to be 1.5% approximately. Around 80% of patients with spinal cord injury (SCI) and myelomeningocele as well as the analatresia patients are suffering from faecal incontinence.

The nerves and muscles of the colon, rectum and anus function together in a closely co-ordinating manner in order to maintain continence.

If some of these functions are out of order or do not work properly, e.g., if a person is suffering from some kind of defect in the control of the anorectum, this person will very possibly be incontinent.

The defects may be a result of a central damage, e.g., mental retardation or old age, or it may be a result of a spinal or peripheral damage, e.g., multiple sclerosis (MS), tumours or metastases, degenerative illness, cauda equina tumour (tumour in the end of the spinal cord-tail), peripheral disease of the nervous system (due to diabetes, MS) or obstetric sphincter rupture.

In addition to surgical treatment of incontinence, faecal incontinence, medication and regulating meal times and defaecation habits, enemas or irrigation are some of the treatments that have been practised for a long time.

Enemas or irrigation may also be used by completely healthy people if they for some reason want to avoid toilet visit for a longer period of time.

For this purpose several devices have been proposed during time. Besides devices especially for the use for performing irrigation for treatment of incontinence, other similar devices have been proposed for irrigation, i.e., products developed for the administration of barium sulphate enema or the like as part of a radiological examination.

U.S. Pat. No. 3,990,448 discloses an enema tip comprising an acorn portion at the end thereof, a distal staff portion connected to the acorn portion and a stop or locator portion connected to the distal staff. The locator portion includes a locator shoulder, which determine the proper degree of insertion of the tapered acorn portion of the enema tip. The enema tip is designed for introduction of a barium enema into the patient. The tip construction is said to provide a location feature itself and is thus said to make it unnecessary for the user to perform this function. Although the optimal diameter of the tip portion is claimed to be ⅞ of an inch (~22 mm) which is to small if the device should be used for irrigation purposes. A simple enlargement of the device would not solve the problem as the pressure from a larger tip of that same material would tend to stress the muscles and the fragile wall of the rectum.

Another product is disclosed in U.S. Pat. No. 3,766,920. This product comprising a smooth, flexible enema tip having an inflatable balloon mounted on the stem behind the exit port from the tip. A limited volume, flexible, hand distendable air resorvoir is connected to the balloon like retention ring so that the operator compression of the reservoir will inflate the ring. As it appears from the description, this device is expected to be operated by a physician or his assistant. There is no indication whatsoever that the user could use this device without help.

U.S. Pat. No. 3,459,175 discloses a device for giving enemata including an inflatable balloon received on a pipe having an undulating outer shape. An additional balloon may be used on the pipe at a location spaced longitudinally of the first balloon. An abutment element may be provided which is mountable on said undulations and is positionable against the patient's anus for blocking flow of fluid out of the patient's bowel. According to an illustrated embodiment, the abutment element is elliptical so that it better fits the space between the buttocks when in use. This device is further provided with means for placing of air and barium into the colon without blowing barium into the colon. According to the description, this device is expected to be used by a nurse or other similar person.

The product disclosed in EP 109 897 A1 is a similar device with a fixation device in the form of a double balloon. One balloon is situated on the internal side of the sphincter and the other is situated on the external side of the sphincter. In this way the sphincter is subjected to pressure from both sides. Again the balloons need to be operated during and after insertion.

Further, GB 2 224 212 A discloses a rather complex rectal insertion device and control valve means therefor. The speculum in the colonic lavage apparatus comprises an elongated tubular body having a tapered leading end provided with a pair of diametrically opposed apertures. The major length of the body tapers rearwardly from the leading end into a trailing end which is coupled to a liquid delivery line from a source of liquid under pressure. If the speculum is to be held the anal canal of the patient, it may be provided with an inflatable cuff. As it appears from the description, this apparatus is a large and complex unit that need to be operated by assistant personnel.

Common disadvantages of the devices described above are that the use of a balloon as fixation member may cause a number of problems. Firstly, there is a risk that a balloon may be overfilled which may result in a rupture, that may cause damage of the fragile wall of the rectum, leakage of the liquid filled content of the colon sigmoideum and rectum and stress of the patient. Secondly, the balloon may leak which will let the air or the content of the balloon leak out. The result of this is that the device suddenly will fall out of the rectum followed by an often unpleasant leakage. As the users of these apparatus often have no sensory function in the rectum they will not register if the device is falling out. Thirdly, the balloons used in these devices are often made from latex. This may cause problems for patients and others suffering from latex allergy. Moreover, specialist have experienced that using a balloon as fixation member is acceptable for use when performing irrigation on children, because their rectum is narrower and not yet damaged from many years suffering from constipation as in many SCI adults. On the contrary, when the irrigation is carried out on adults there is a tendency that the balloon is not a very effective fixation member. When filling the balloon with more air in order to overcome the fixation problem, the balloon expands in both radial and axial direction. When expanding in axial direction the balloon may cover the eyes of the catheter, thus stopping the flow. When having to perform irrigation on small children a further problem arises because the devices commercially available today are rather large, they therefore seem rather scary both for the small children and for their parents. The existing products do not appear pleasant due to their size and colour.

All the above mentioned products have the further disadvantage that they do only disclose embodiments where the fixation member is placed very close to the sphincter and where the eyes of the catheter are positioned in rectum. Still further, the mentioned products are too expensive to use as disposable products. According to specialists these products are used several times for the same patient, while being cleaned in-between, this cleaning also being time consuming. Despite the cleaning in-between, the person skilled in the art will understand that there is a larger risk of contaminating the environment during storage of the product inbetween each use, compared to the use of a disposable product.

Finally, the devices for irrigation are often large and complex apparatuses, that are too expensive for the user to have at home and often need to be operated by an assistant.

Therefore, the above mentioned products do not fulfill the requirements of the users of irrigation devices.

The rectum is a very delicate part of the human body and it is required that it is protected from abrasion, perforation, infection as well as excessive pressure. Accordingly, any device which is intended for rectal insertion should not have any tendency to abrase or perforate the rectal wall even if coming into contact with the wall during insertion and must especially not have any sharp edges.

In order to ensure a high fulfillment of the users' needs, it is further of utmost importance that the device for irrigation is very easy and safe to use. In other words, the device should be very simple to apply, the appearance of the device should not be scary to the user, it should not slip out during use, it should never leak, it should be secure against leakage, easy to get rid of after use, e.g., be disposable in the conventional systems in order to avoid cleaning, and it should be possible to position the eyes of the catheter based on the need, not only in rectum but also in colon sigmoideum and colon descendens.

The device for irrigation according to the present invention offers all these above mentioned features and advantages.

SUMMARY OF THE INVENTION

The object of the invention is to provide an irrigation device that will overcome all the disadvantages connected to the known products and render an irrigation simple and easy to perform. There is a high need for a device that solves the problems of the fixation member, provides for security against leakage problems, and, at the same time, can be used by both children and adults, without being scary in its appearance. A further object of the invention is to provide a disposable device in order to overcome infection problems and being time saving. Finally, the device should be easy to apply in order to avoid the need for an assistant. In other words the irrigation device according to the present invention will give the user a higher quality of life.

BRIEF DESCRIPTION OF THE DRAWINGS

Below embodiments of an trans-anal irrigation device according to the invention and components of same will be explained in more detail with reference to the drawings, in which.

The drawings are all schematic examples of specific embodiments of the invention and are not to be considered as being limiting for the scope of the invention being defined by the appended claims.

DETAILED DESCRIPTION OF THE INVENTION

The invention relates to a device 1 for irrigation of externally debouching, natural or artificial body canals 21 of animals or human beings and comprising a catheter 2, and optionally a container 3 designed for containing an irrigation medium 4 and a tube member 5 connecting the catheter 2 with the container 3, which device is characterised in that the catheter 2 is provided with a fixation member 6 for fixation of the catheter 2 inside the body canal 21 and for providing a liquid tight seal between the catheter 2 and the body canal 21, which fixation member 6 automatically fixates the catheter and seals between the catheter 2 and the body canal when placed in the body canal 21.

The advantage of this embodiment is that a more secure fixation is obtained, thus minimising the risk of leakage.

Figure 1:
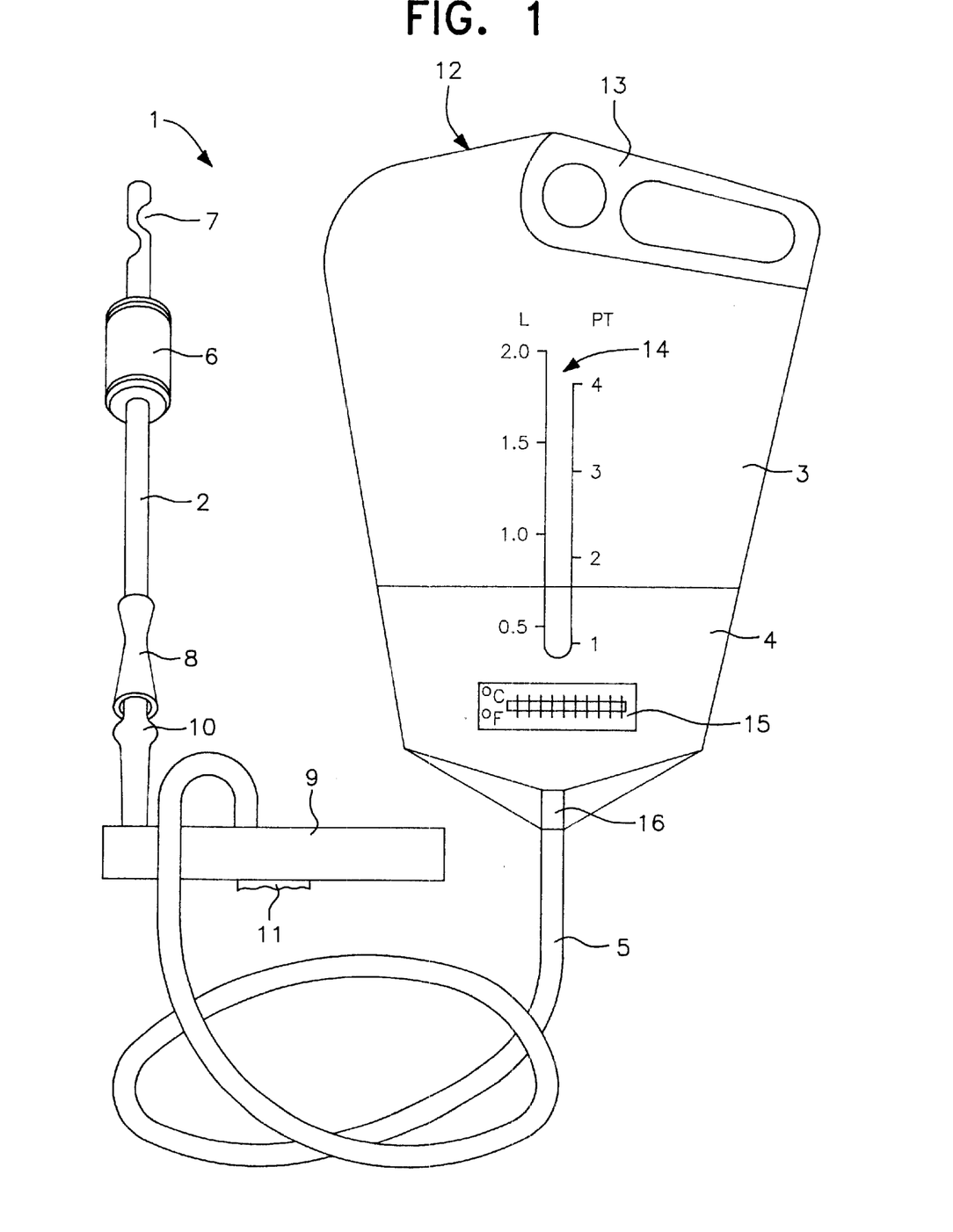
FIG. 1 illustrates a complete irrigation device according to a first embodiment of the invention.

A first embodiment of the invention is illustrated in FIG. 1. The catheter 2 is a conventional female or male urinary catheter, that is hollow and is provided with one or more of eyes or opening 7 and a connector part 8. Other kinds of catheters may also be used. The numbers of eyes are chosen according to the actual need and in this embodiment two eyes are chosen. The edges of the eyes may optionally be rounded in a suitable process, e.g., heat treatment in order to avoid cutting or snagging down haemorrhoids during extraction. The catheter 2 is via a tube member 5 connected to a container 3, containing an irrigation medium 4. The tube member 5 is optionally provided with a flow regulation member 9 comprising a connector tube 10 for connecting the catheter 2 via the connector part 8, a manual regulated button 11 for regulating the flow before or during use. The container is provided with opening means 12 for the filling of irrigation medium 4 and with handle means 13 for holding and/or suspending the container 3. The container 3 is further provided with measuring means 14 for measuring the volumetric content of irrigation medium 4 and with temperature measuring means 15 in order to enable the user to measure the temperature of the irrigation medium before introducing it. The container 3 and the tube member 5 with the flow regulation member 9 is connected at 16. The tube member 5 of the container 3 is connected to the catheter 2 before use. After use the tube member 5 is disconnected, the catheter is thrown away and the container may be reused.

In a preferred embodiment of the invention the fixation member 6 is made of compressible material. This compressible material may, e.g., be a foam or a moulded elastic material.

With this embodiment the irrigation device 1 can be inserted in the rectum 21 using only one hand. This is an advantage compared to known embodiments using a kind of balloon as fixation member, where the irrigation device has to be positioned with at least one hand at the same time as the balloon is inflated with air by use of at least one hand. The device 1 according to the present invention does not necessarily require extra assisting personal, when the user wants to perform the irrigation. The fixation member 6 can be made of a material that needs to be wetted before insertion or another material that can be used directly without wetting.

In another preferred embodiment of the invention the fixation member 6 comprises a resilient compressible plug-like body of moulded material, which body, when inserted into the body canal, is self expandable to a cross-sectional dimension ensuring closure of the body canal 21, 22.

When using this embodiment a device 1 for irrigation is obtained in which the fixation member 6 may be very small before being inserted. The result is a device 1 with a quite harmless appearance compared to devices with extra tubes and air providing members for the filling of the fixation balloon.

It is preferred that the fixation member 6 is kept in a compressed state before insertion by a film material 24.

This is a particular advantage as the film when the device is inserted will quickly dissolve when coming into contact with the warm humidity of the rectum and the fixation member 6 will expand. Other film dissolving or removing methods, like, e.g., pH activating system may as well be used.

The film material can be any materials known per se for this use, e.g., polyvinylalcohol (PVA) film, which will dissolve when getting into contact with humidity.

Figure 2:
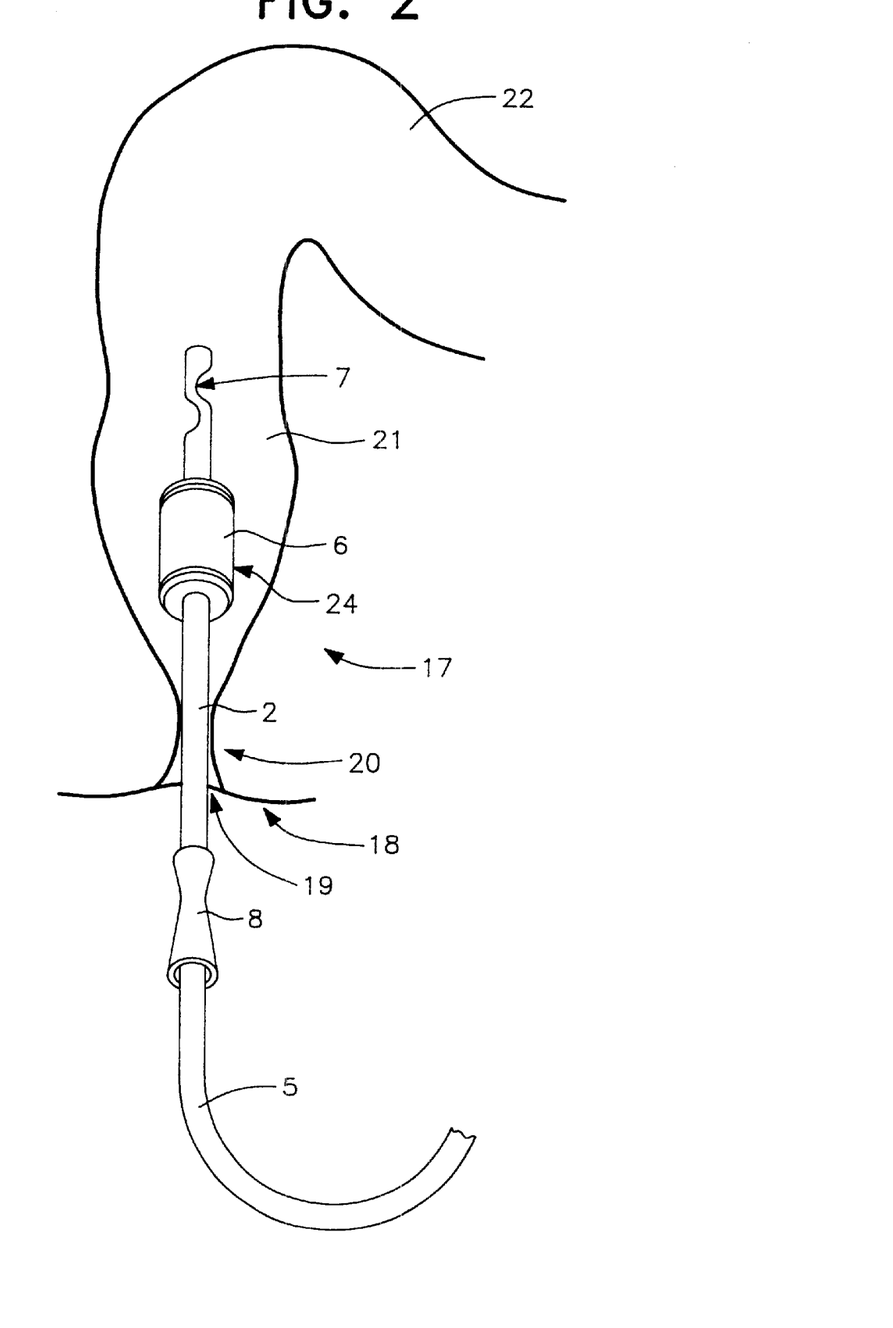
FIG. 2 illustrates in cross section a normal rectum and part of the colon sigmoideum from a human being and a detail of an irrigation device according to a second embodiment of the invention.
Figure 3:
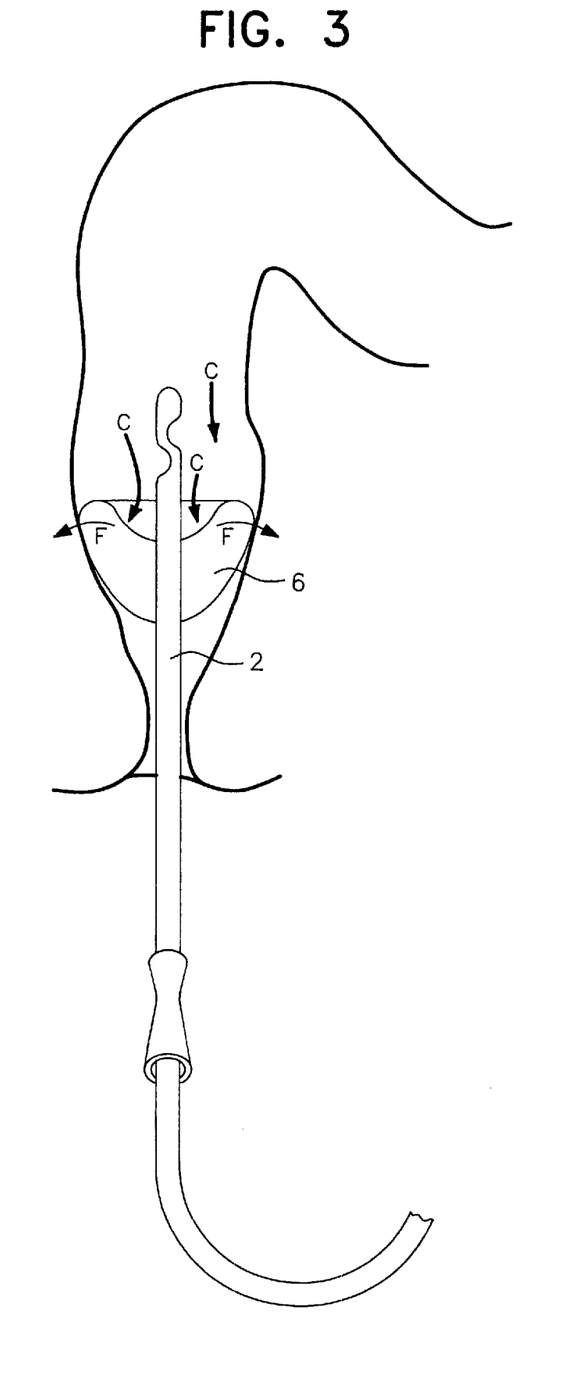
FIG. 3 illustrates the embodiment according to FIG. 2, with the fixation member in expanded condition.
Figure 9:
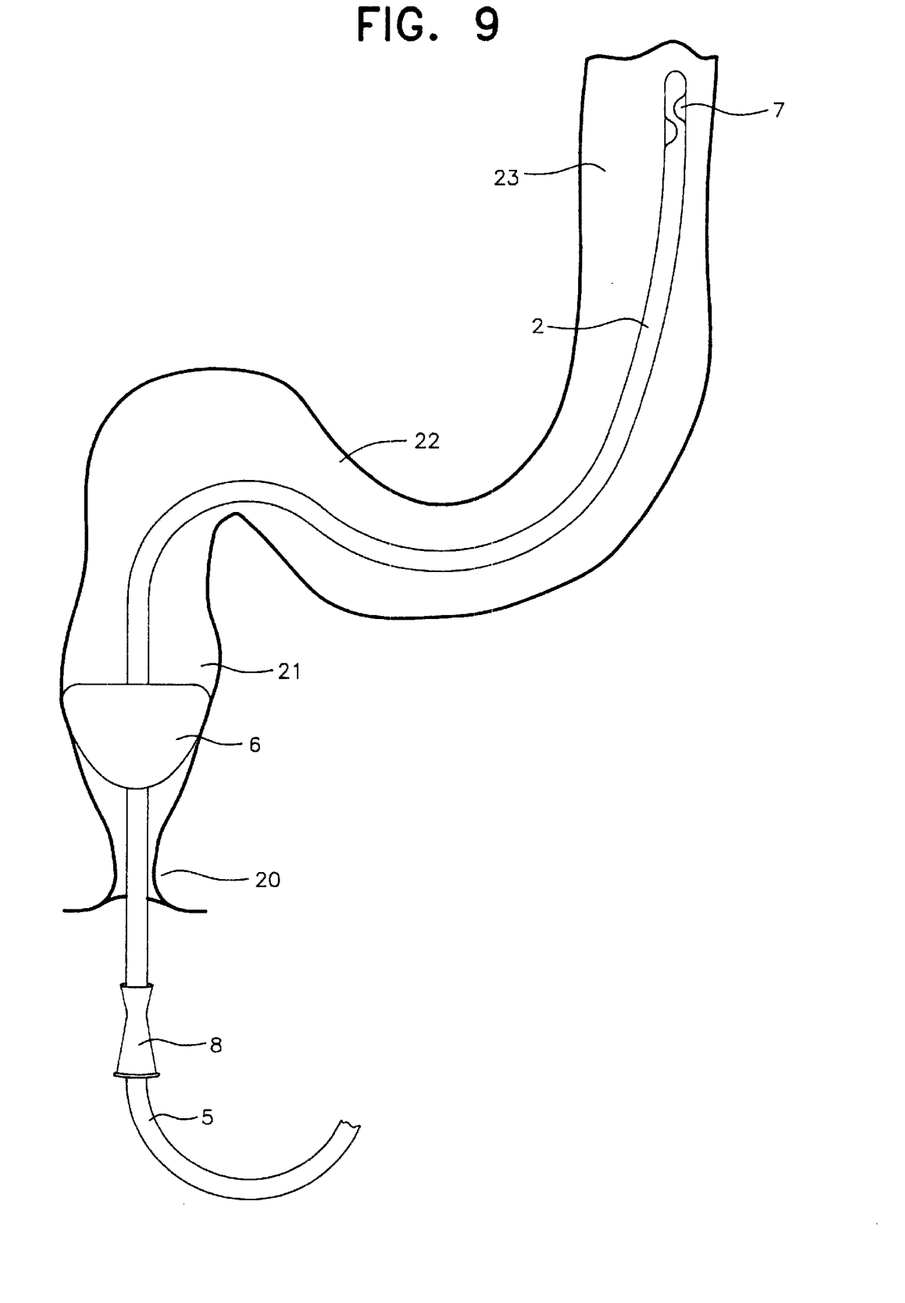
FIG. 9 illustrates in cross section the rectum, the colon sigmoideum and the colon descendens with an irrigation device according to a seventh embodiment of the invention.

In FIG. 2 and FIG. 3 an embodiment of the above mentioned type is shown. FIG. 2 indicates in cross section the anal canal area 17 of a human being. The external surface 18 and the orifice 19, through which the catheter 2 is inserted. When inserting the catheter with the fixation member 6 the user has to push it through the sphincter 20. In FIG. 2 the catheter is placed with the fixation member 6 located in the rectum just inside the sphincter 20. The catheter 2 is a short catheter, having its eyes 7 located in the level of rectum. As it is shown in FIG. 9 the catheter may be much longer and extend through rectum 21, colon sigmoideum 22 and colon descendens 23, and having the eyes 7 located in the top of colon descendens in order to establish the inflow at a higher point. This may be wanted if, e.g., there is some severe constipation in colon sigmoideum 22. In this case the fixation member 6 may be displaced along the catheter 2.

The fixation member may also be provided with an internal sleeve, that could be displaced along the catheter together with the fixation member. In this case the catheter may further be provided with a one way lock system ensuring that the fixation member can only be displaced in one direction.

In the embodiment shown in FIG. 2 the fixation member 6 is kept compressed by a film of PVA. When the fixation member 6 comes into contact with the humidity of the rectum the PVA film will start to dissolve and the fixation member 6 will expand. After about 1 to 2 minutes the fixation member 6 has fully expanded, as it is shown in FIG. 3, and the irrigation may begin. The shape of the fixation member 6 with a bowl shaped top surface will safely prevent leakage. The arrows marked C in FIG. 3 illustrates the situation if some of the content in the rectum 21 tries to push the fixation member 6 downwards. The content will fill up the bowl shaped top surface and the sides of the flexible fixation member 6 will be pushed towards the walls of the rectum, the arrows F, thus providing an even better liquid tight seal between the catheter 2 and the rectum 21. The function of this kind of fixation member 6 is the same whether it is placed in the rectum 21 or further up in the colon sigmoideum 22.

Figure 4:
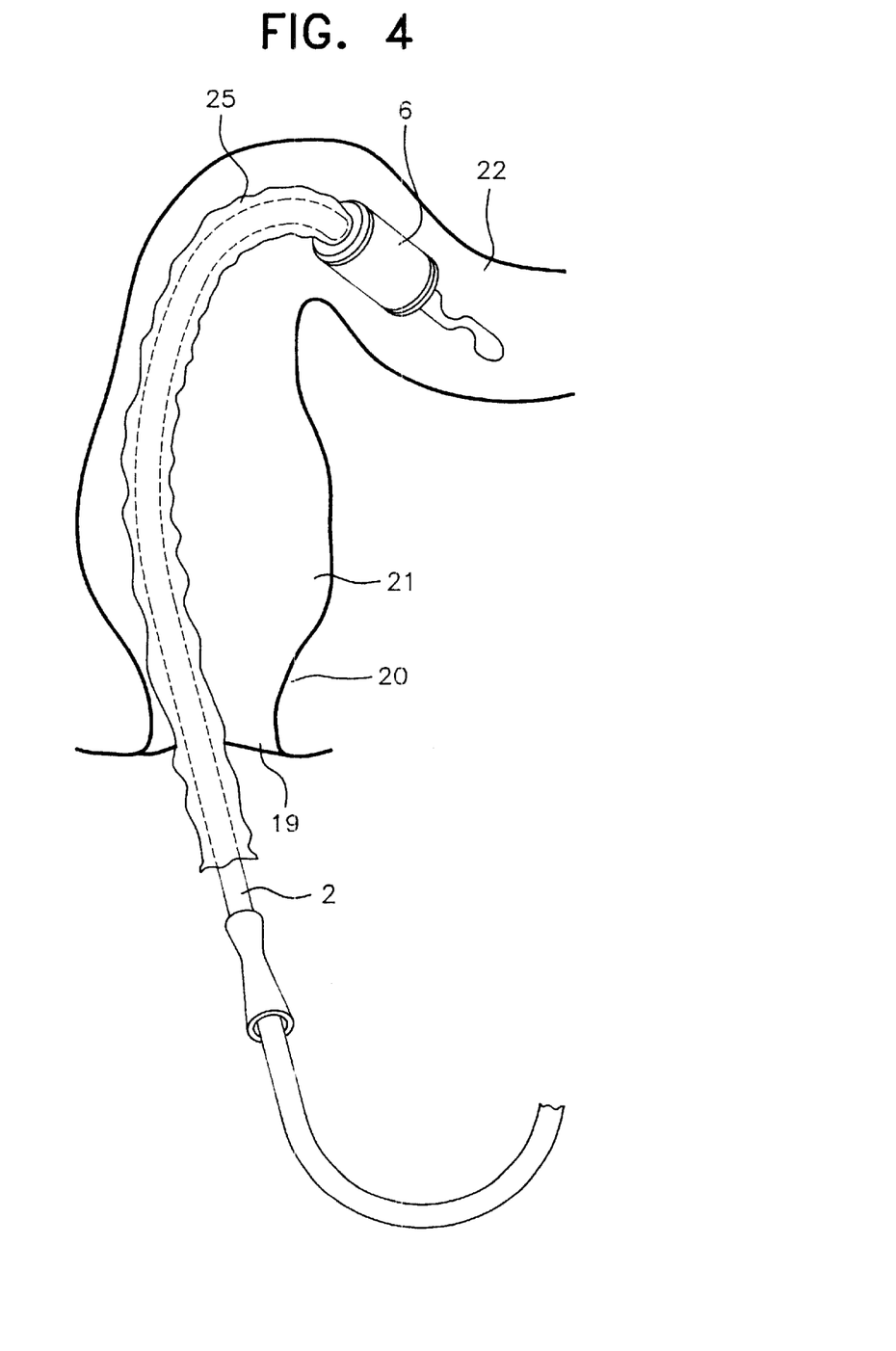
FIG. 4 illustrates in cross section an abnormal rectum and part of the colon sigmoideum from a human being and a detail of an irrigation device according to a third embodiment of the invention.

FIG. 4 illustrates in cross section an abnormal rectum 21 and part of the colon sigmoideum 22 of a human being and a detail of an irrigation device 1 according to the invention. The orifice 19 is constantly open and the sphincter 20 is out of function. The internal volume of the rectum is abnormal huge and the walls are flaccid. The embodiment shown in FIG. 4 is characterised in that the catheter is quite long and that the fixation member can be displaced in relation to the catheter. In order to prevent the fixation member 6 from staying inside the person when the catheter 2 is extracted the fixation member 6 is provided with a cord of gauze 25. The advantage of this embodiment is that the fixation member 6 when placed in the colon sigmoideum 22, closes the system and irrigation is possible. With a dilated rectum 21 as shown in FIG. 4 it would not be possibly to perform a normal irrigation without huge leakage or it would be necessary to use strong and unpleasant adhesive means in order to close the orifice 19 of the person while performing the irrigation.

Figure 5:
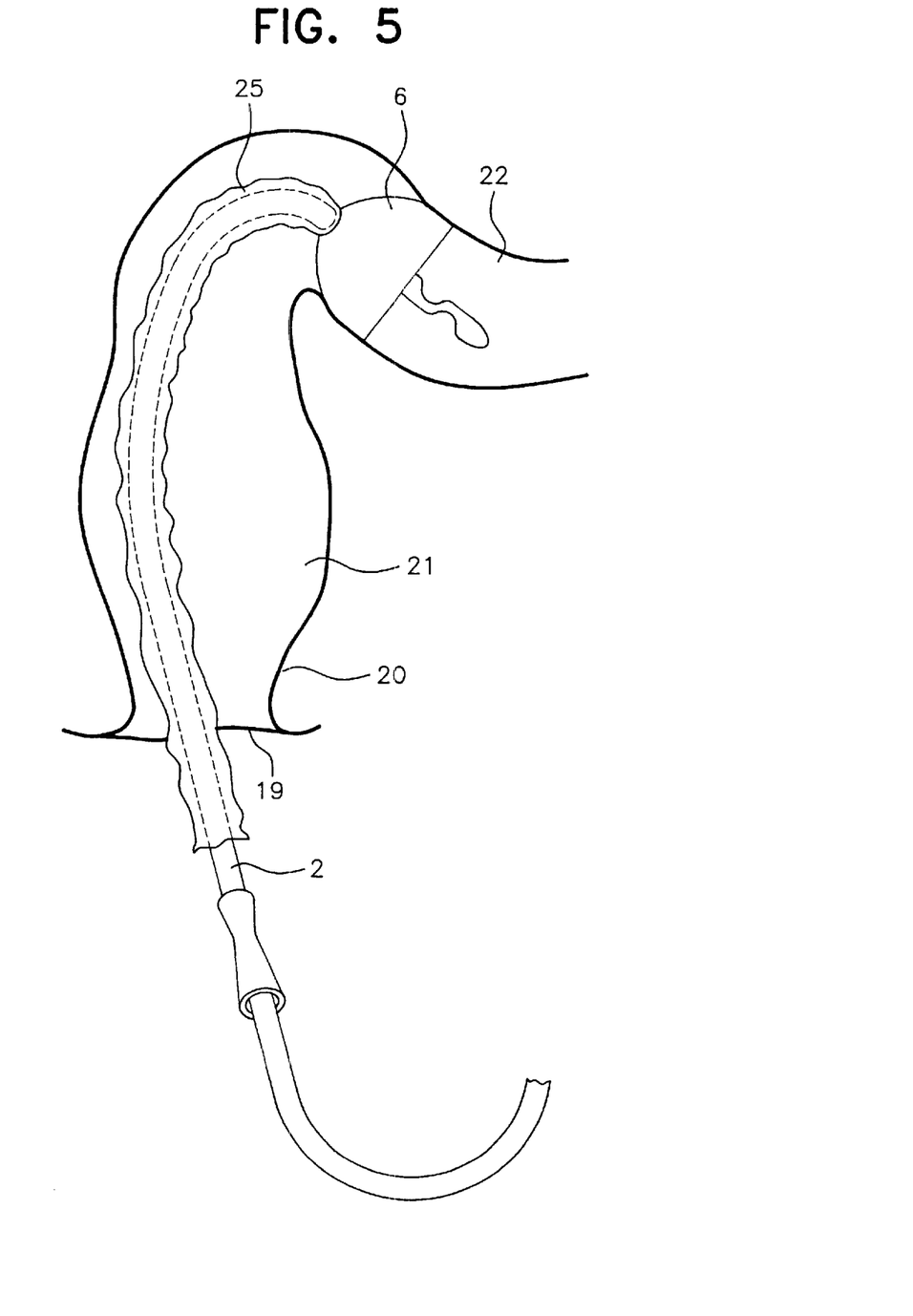
FIG. 5 illustrates the embodiment according to FIG. 4, with the fixation member in expanded condition.

FIG. 5 illustrates the embodiment according to FIG. 4, with the fixation member 6 in expanded condition.

A further preferred embodiment of the invention is characterised in that the fixation member 6 is kept in its compressed state by an applicator. This a well known method of inserting devices that is intended to expand later on. The applicator may be in the shape of a tube member, in either essencially hard material, or some kind of soft film material.

Figure 8:
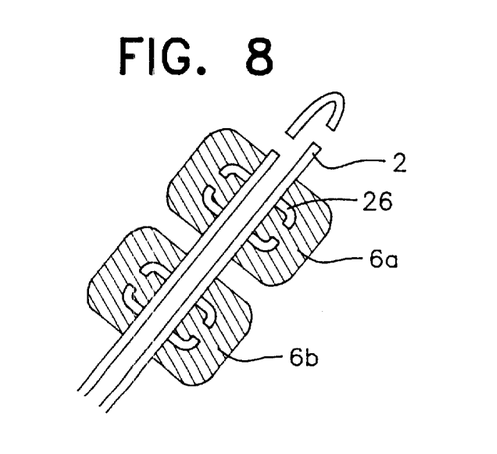
FIG. 8 illustrates a detail of an irrigation device according to a sixth embodiment of the invention.

An embodiment with members 26 extending from the surface is shown in FIG. 8 and acts as a mechanical lock for the fixation member 6. Such members may be in the form of flanges, ribs or arrows or hooks.

Figure 6:
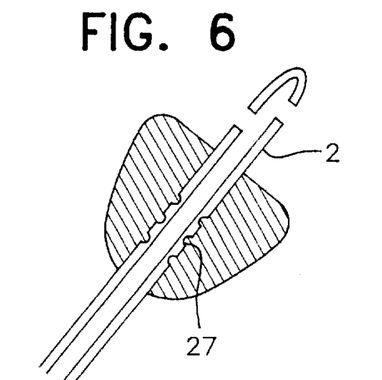
FIG. 6 illustrates a detail of an irrigation device according to a fourth embodiment of the invention.

The extending members 26 may have any shape, and be of any numbers. They may be formed as an integral part of the catheter 2 or they may be provided on the external surface of the catheter 2. This embodiment ensures an extra contact force between the catheter 2 and the fixation member 6. The extra contact force may also be provided by some indentations or grooves 27 made in the external surface of the catheter 2. This is shown in FIG. 6.

A still further preferred embodiment of the invention is characterised in that the fixation member 6a, 6b comprises more than one part. This embodiment is shown in FIG. 8. In some cases the rectum 21 or the sphincter 20 may have a shape that requires use of fixation member 6 comprising several fixation parts in order to be sufficient effective. In this case all the parts 6a, 6b can be located inside an applicator or can be covered separately by film material 24.

In a further preferred embodiment of the irrigation device 1 the fixation member 6 is an anal plug known per se as the one disclosed in WO 95/28138. One embodiment of a known anal plug has been illustrated in the FIGS. 1, 2, 3, 4, 5 and 9.

This embodiment is in practice particularly advantageous as the users are often already familiar with using anal plugs as well as catheters for catheterisation. The device according to this embodiment is therefore more easily accepted and much less scary as it comprises parts well known to the users.

Furthermore it is preferred that the fixation member 6 of the invention is an anal plug that is essentially conical.

This embodiment has shown its efficiency in practice. Having a conical shape with the tip of the cone in the direction of the sphincter 20 and the larger diameter in the direction of colon sigmoideum 22 and especially when the conical plug further is provided with a bowl like top surface, as explained in the description of FIG. 3, the fixation member 6 is very effective. When the content of the colon sigmoideum 22 or the rectum 21 actuate pressure on the top surface, the fixation member 6 will tend to enlarge the diameter, thus fixating even more efficiently. Having a conical shape with the smaller diameter tapering towards the rectum the risk of the fixation member coming into contact with the sensory areas just above the sphincter is avoided. Touching of these sensory areas by conventional fixation members as a balloon could result in either a very active peristaltic movements with a considerable risk that the fixation member is pushed out or the balloon colud also result in an inhibiting action on the above mentionend sensory areas and thereby an inhibiting action on the peristaltic movements.

Figure 10:
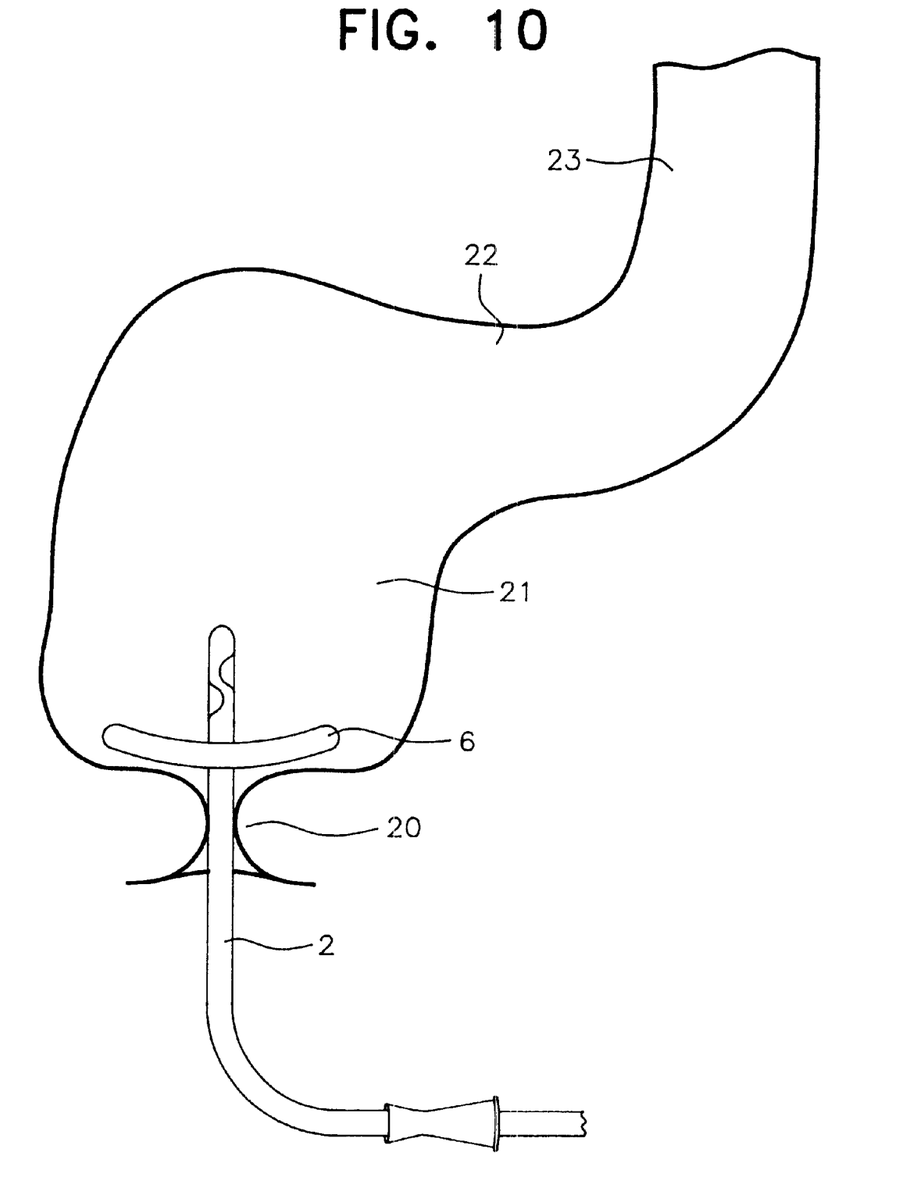
FIG. 10 illustrates in cross section the rectum, the colon sigmoideum and the colon descendens of a person with a dilated body channel and an irrigation device according to an eighth embodiment of the invention.

Some persons suffering from dilation may need a larger fixation member. FIG. 10 illustrates in cross section a person with a dilated rectum area 21, and an essentially normal colon sigmoideum 22 and colon descendens 23. A catheter 2 is placed with a fixation member 6 located in the rectum just inside the sphincter 20. The fixation member used in FIG. 10 is larger and more flat than e.g. the fixation member 6 shown in FIG. 9, in order to prevent leakage of material from the dilated rectum.

Figure 11:
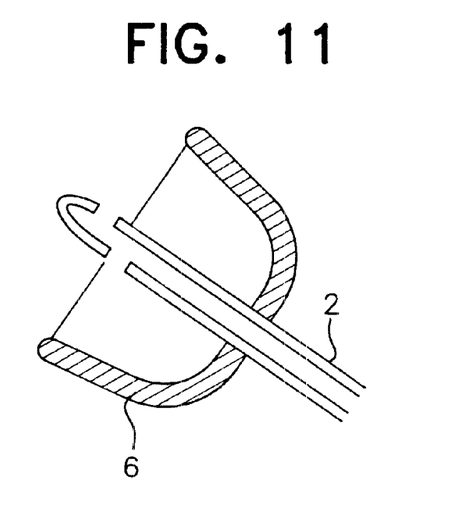
FIGS. 11–15 illustrate different embodiments of the fixation member according to further embodiments of the invention.

FIGS. 11–15 are examples of different embodiments of the fixation member according to the invention. In FIG. 11 the fixation member 6 is bowl-shaped and may have a rather large diameter when in unfolded position. This shaped is used for some kind of dilated rectum. Only when the product is extracted, the walls of the fixation member 6 will tend to collapse making it easier to extract the product.

Figure 12:
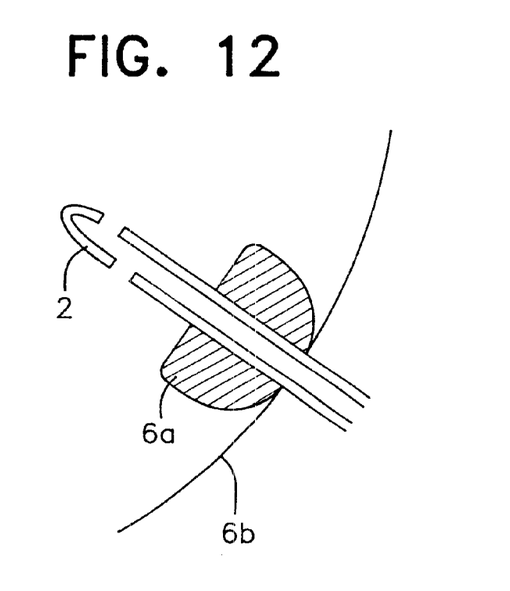
Figure 13:
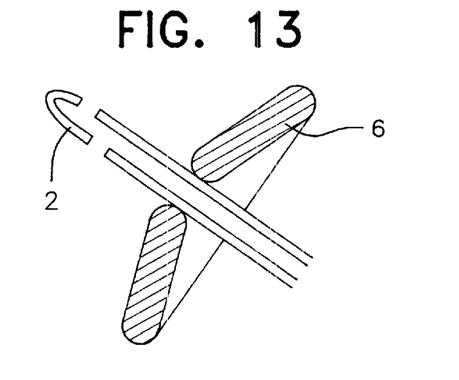
Figure 14:
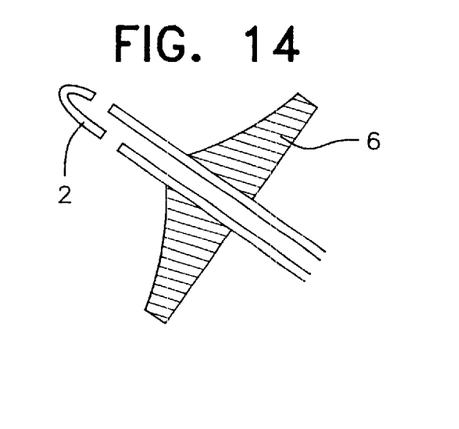
Figure 15:
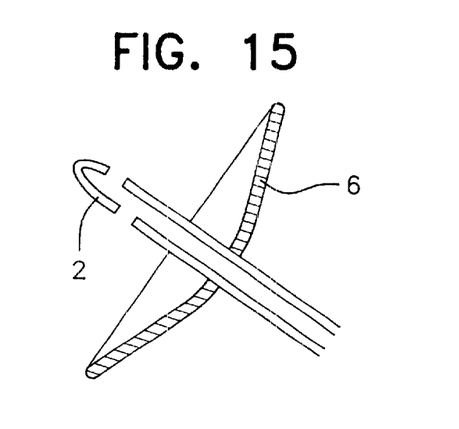

The fixation member may be reinforced by providing it with ribs or other reinforcing structures as different wall thicknesses as it appears in FIG. 14. Part or parts of the fixation member may also be manufactured in another material. This other material could be in a harder material for reinforcing reasons. It could also be a plate 6b of film material provided beneath and connected with fixation member 6a as shown in FIG. 12. This plate of film material is provided in order to prevent leakage from a dilated rectum. Other embodiments of the fixation member preventing leakage are shown in FIGS. 13 and 15.

In a further preferred embodiment of the invention the fixation member 6 is provided with handle means in the form of extraction members 25. The extraction means 25 can be any kind of soft and flexible material. It can be made from a material with a knitted structure. Further it may be an element of woven or non-woven material, preferable fabric or plastic. It may be designed as a stocking-like element and it can be of gauze. In a preferred embodiment, the handle means are integrated with the fixation member as disclosed in WO 95/28138.

Figure 7:
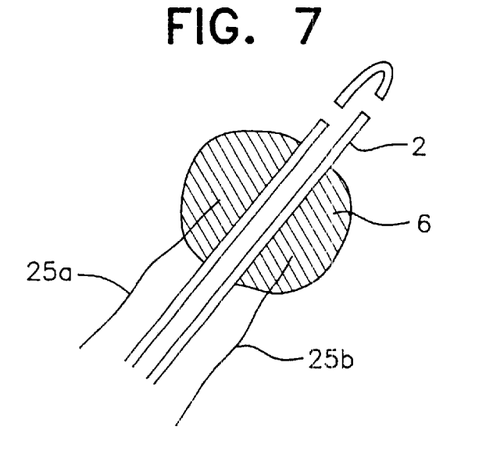
FIG. 7 illustrates a detail of an irrigation device according to a fifth embodiment of the invention.

The embodiment in FIGS. 4 and 5 is shown with means 25 for withdrawal of the device in the form of gauze and the embodiment in FIG. 7 is shown with the extraction member 25 in the shape of two bands 25a, 25b fixated inside the fixation member 6.

The irrigation medium 4 to be used with the irrigation device of the invention can be any suitable medium, e.g., tap water, sterile water or oily substances. Substances containing barium sulphate and the like for radiological purposes may also be introduced into the rectum using the irrigation device of the invention.

The flow from the container through the tube member may be controlled by a traditionally valve system known per se. The tube member 5 of the irrigation device shown in FIG. 1 is provided with a flow regulation member 9. The flow regulation member 9 may also be placed close to the container 3.

The catheter may further be provided with a stop member for indication of the length to be inserted into the rectum. This stop member may have the form more or less like a circular plate and may be made of absorbing material in order to absorb a leakage, although leakage should not under normal circumstances be possible with the device according to the present invention. The catheter may also be provided with numbers or other indication marks for indication the depth.

The tip of the catheter 2 and/or the tip of the fixation member 6 may be provided with some kind of lubricant, like vaseline or the like, in order to ease the introduction of the catheter through the sphincter 20 and into the rectum 21. The tip of the catheter may also be protected by a sleeve in order to avoid contamination.

A second aspect of the invention relates to a method of producing a device (1) for irrigation of externally debouching, natural or artificial body canals 21 of animals or human beings, and is characterised by the steps of providing a catheter 2, moulding the fixating member 6 around it, connecting the catheter via a tube member 5 to a container 3 designed for containing irrigation medium 4.

Instead of moulding the fixation member 6 and the catheter 2 together they could be glued together or the catheter 2 could simply be pushed through a hole in the fixation member 6. Such hole preferably has a diameter allowing for passage of the catheter and yet ensuring a sufficiently light connection to avoid leakage.

The method could further comprise the steps of compressing the fixation member 6 and providing it with a PVA film 24, or the like, or placing it together with the catheter 2 in an applicator, optionally in a more or less compressed state. Such an applicator may, e.g., be an applicator like those normally used together with hygienic absorbing articles such as tampons.

A third aspect of the invention relates to the use of a device 1 for performing irrigation of externally debouching, natural or artificial body canals of a person, comprising the steps of insertion of a catheter 2 with a fixation member 6 in the rectum 21, lifting a container 3 connected to the catheter 2 via a tube member 5 above the level of the body canal 21 and emptying the content 4 of the container 3 through the tube member 5 and the catheter 2 and into at least rectum 21, colon sigmoideum 22 and colon descendens, 23, waiting for a span of time between 3 and 30 minutes and finally removing the catheter 2 together with the fixation member 6 from of the rectum 21.

The length and the diameter of the catheter 2 as well as the numbers and design of the eyes 7 of the catheter can be chosen according to the actual need. Normally the length from the fixation member to the tip of the catheter is between one and a few centimeters and in most cases the inflow of irrigation medium will take place in the rectum. In some cases it may be desired to provide the inflow of irrigation medium above rectum level, somewhere in the colon sigmoideum 22 or in the colon descendens 23. In these cases the device for irrigation may be provided with a longer catheter, having for example the length of up to 28 centimeters. The length of the catheter 2 from the sphincter 20 to the connector part 8 will depend on the patients need to be able to see the connection site between the catheter 2 and the tube member 5.

Generally when using a catheter with rounded edges of the eyes 7 the risk of pulling down or snagging haemorrhoids or damaging the sphincter during removal of the catheter 2 at the end of the procedure is diminished.

Other combinations of shapes and materials are regarded as to be within the scope of the invention.

Several embodiments have been described with reference to the drawings. The container 3 may be made in any predetermined size according to the needs. Generally, the maximum volume of the container is up to about 2 liters. For special purposes larger containers may be provided. The length of the catheter will mainly depend on the depth of insertion and whether the user wants to be able to see the connector part 8 of the catheter. The container may be provided with different handle parts for holding or hanging the container 3 in different positions, or it may be provided with double sided adhesive for the same purpose. Further, the container itself may be provided with instructions for the user. The disposable catheters 2 comprising the fixation member 6 may be packed in a packaging containing several units. The packaging may be provided with instructions for the user.

A user, who wants a life as independent of assistance from other persons as possible, needs a simple and easily operable system comprising all the parts for performing the irrigation as an integrated unit. The system according to the present invention offers these features. It is very easy to use and handy to carry along. The user may insert the catheter either in sitting, lying or standing position and wait one or two minutes while the fixation member expands and then placing the container with the flow regulation member on a hanger above rectum level. Once positioned on the toilet the user makes the water enter by regulation the inflow velocity. When the water has been acting for certain amount of minutes, the user simple and gently pulls the device out again and the faeces will exit. In between use of the trans-anal irrigation device the user have the option to wear a normal anal plug in order to feel completely secure, but in most cases this is not needed as long as the irrigation is repeated two or three times a week.

The irrigation device 1 has been described by way of example for the use for trans-anal irrigation purposes on human beings. The irrigation device according to the present invention may as well be used for administering barium sulphate and the like for radiological purposes, and for administering of medicine in general. In these cases the container may be different from the container described with reference to the drawing. Finally the irrigation device may as well be used on animals.

MATERIALS AND METHODS

The materials and processes used for the production of the parts of the irrigation device are conventionally used materials and processes known by the person skilled in the art.
The catheter:

The catheter is a conventional, hollow female or male urinary catheter. The catheter could be made of any flexible material, preferably a polymere and most preferably plasticized PVC. Size and length of the catheter could of any suitable dimension between Ch 8 and Ch 40 and 15 cm to 60 cm. The catheter could be non-coated or coated with an hydrophilic layer.
The fixation member:

The fixation member could be made of any material processed as a foam, preferable polyurethane (Hypol®). The fixation member made of Hypol® could be performed with an open or a closed structure. In the present invention the fixation member has an open structure to allow air passing through during irrigation.

The fixation member is compressed and wrapped in a PVA film or other suitable film material. The compression rate is calculated to ensure the material to expand into its virgin dimensions after removing or dissolving the PVA film.

If the fixation member is provided with some kind of reinforcing structures. These could be ribs made of the same material as the fixation member it self, or it could be different kinds of elements made of another suitable material and connected to the fixation member either during the processing of the fixation member e.g. mechanically or chemically, or afterwards by using, e.g., glue.

The fixation member is provided with means to ensure removal from rectum after use. This removal means could be of any soft yet strong material, preferable gauze.
The container:

The container could be made of any waterproof materials, preferable plasticized PVC.
The tube member:

The tube member could be made of any flexible material, preferable plasticized PVC to prevent the tube to kink.
The optional flow regulator:

The flow regulator is provided with a handle to secure a proper operation. Inside the handle (house of the valve) a finger operated valve is placed. The valve consists of the flow regulating valve and a spinning wheel to monitoring the flow. All components could be made of dimension stable plastic, preferable polycarbonate (PC) or polyacrylnitrilbutadienestyrene (ABS). The monitoring of flow could be either mechanical or digital.
The optional thermometer on the container:

The thermometer could be a conventionally mercury thermometer or preferable a fluid crystal thermometer.

In case of patients with myelomeningocele the device may not include natural rubber.
Methods:

When producing the irrigation device the catheter may be pushed through the anal plug. The material of the anal plug may also be moulded around the catheter. Further the catheter may be provided with extending parts either integrated with the catheter or mounted after production of the catheter. These parts may form a mechanical locking member for the anal plug, when it is moulded around the catheter. The catheter and the fixation member may also be formed as an integrated unit of the same material.

The container is connected with the tube member, e.g., by gluing or preferably by welding, using, e.g., a heat welding machine e.g. an impulse welding machine or an HF welding machine.

EXPERIMENTAL PART

The invention is explained more in detail below with reference to the Examples disclosing embodiments of the present invention. The examples are not considered to be limiting to the scope of the invention which is defined in the appended claims.

Production of an Irrigation Device According to the Present Invention

Example 1

The fixation member was moulded by a foaming process. The material was a polyurethane (Hypol®). Before starting the foaming process a catheter made of plasticized PVC Ch 18 with the length of 150 mm was placed in the mould. Then the foaming process was carried out. The shape of the mould and the fixation member corresponding the shape of the anal plug commercially available under the trademark Conveen® Anal Plug. The result was a strong contact force between the catheter and the fixation member. After moulding the fixation member was compressed and covered by a PVA film that is dissolvable when coming into contact with humidity. The external end of the catheter was connected to a container via a tube member. The irrigation device was used and pulled out after use. The contact force between the catheter and the fixation member was strong enough to ensure the extraction from the rectum after use.

This process could also have been carried out with catheters of different sizes e.g. from Ch 8 to Ch 30, and with different lengths—female and male catheters, without having to change the process. The material of the catheter may be any suitable essentially soft and flexible material.

If even larger forces is wanted the catheter could have been provided with external extending gripping members in order to ensure a mechanical lock between the catheter and the fixation member after it has been moulded around the catheter.

Example 2

In this example the fixation member was first moulded with a handle part in the shape of a cord of gauze. The material and the shape was the same as of example 1. Then a hole was provided in the fixation member by a cutting process. The hole could as well have been provided either during the moulding process or by a punching or similar process. The catheter was forced through the hole of the fixation member. There was used a catheter Ch 20 and with a length of 36 cm. The fixation member was like in example 1 compressed and covered by a PVA film.

When performing the irrigation with the device according to example 2 the user can choose in which height in the rectum, the colon sigmoideum or the colon descendens the irrigation is wanted. It is possible to displace the catheter and the fixation member in relation to one another. After use the catheter and the fixation member is extracted by pulling the cord of gauze and the catheter at the same time.

If the displacement of the fixation member in relation to the catheter is not wanted the catheter and fixation member can simply be glued together.

Use of the Irrigation Device of the Invention

A device comprising a small anal plug as fixation member and a Ch. 18 female catheter was inserted into the rectum of a child. The child was standing while the catheter was inserted and sat down on the toilet afterwards. Before insertion the tip of the catheter and the top of the plug was lubricated with vaseline. When the catheter with the plug was inserted the plug was positioned just inside the sphincter. After 2 minutes of waiting while holding on to the catheter the PVA-film of the plug was dissolved and the self expandable plug had expanded and was now closing the rectum. The container with irrigation medium, in this case tap water, approximately 30° C., and the tube member was connected to the catheter.

The patient performed the irrigation with one liter of 30° C. warm water with a flow rate of 100 ml/min. The flow was registered by a stop watch and monitored on the flow regulator. Then the patient waited for 15 minutes before removing the irrigation device from the rectum by pulling gently in the catheter and the cord of gauze. The irrigation water and the faeces was now emptied from the rectum into the toilet.

The amount of irrigation medium, the flow rate and the temperature of the irrigation medium as well as the sizes of the catheter and the fixation member are all individually parameters.

What is claimed is:

1. A device for irrigation of externally debouching, natural or artificial body canals of animals or human beings comprising: a catheter provided on an outer surface thereof with an annular fixation member, said fixation member being made of compressible material in the form of a resilient externally compressed plug-like body of moulded material that is self-expandable, said fixation member being externally compressed against a catheter, without fluid communication therebetween, by a covering film material that dissolves upon exposure to humidity, said fixation member self-expanding upon dissolution of said covering film material such that both expansion and compression of said fixation member are effected without fluid communication between said catheter and said fixation member.

2. The device according to claim 1 wherein the fixation member has a bowl-shaped top surface when expanded such that a center area of said top surface is recessed relative to edge areas of said fixation member.

3. The device according to claim 1, said catheter including members extending from the surface of the catheter and forming a mechanical lock for the fixation member.

4. The device according to claim 1 wherein the fixation member is in the form of a relatively soft, elastic, open-cell polymer foam.

5. The device according to claim 4 wherein the polymer foam is a polyurethane foam.

6. The device according to claim 5 wherein the fixation member is a conical anal plug.

7. The device according to claim 1, said fixation member including an extraction member for withdrawal of the device.

8. A method of producing a device for irrigation of externally debouching, natural or artificial body canals of animals or human beings, comprising the steps of: providing a catheter, molding a fixation member made of a compressible material around the catheter in a selected position such that there is no fluid communication between said fixation member and said catheter, externally compressing the fixation member, and covering the compressed fixation member with a wrapping made of a film material which dissolves upon exposure to humidity, said fixation member being self-expandable with or without moisture upon removal of said wrapping.

9. A method for performing irrigation of externally debouching, natural or artificial body canals of a person, using a device having a catheter provided with an annular fixation member made of a resilient compressible molded material that is self-expandable, comprising the steps of:

inserting a catheter with a fixation member compressed by a covering film material which dissolves upon exposure to humidity in the rectum of said person;

allowing said film material to dissolve and thereby release said fixation member to expand and thereby provide a tight seal between the catheter and the rectum, said fixation member when expanded having a bowl-shaped upper surface;

lifting a container connected to the catheter via a tube member above a level of the rectum and emptying a content of the container through the tube member and the catheter and into at least rectum, colon sigmoideum and colon descendens;

waiting for a span of time between about 3 and 30 minutes and finally removing the catheter together with the fixation member from the rectum.

10. The device according to claim 3, wherein said extending members include at least one of flanges, ribs, arrows or hooks.

11. The device according to claim 7, wherein said extraction member is made of a soft and flexible material with a knitted structure.

12. The device according to claim 7, wherein said extraction member is made of a soft and flexible material including at least one of plastic and fabric.

13. The device according to claim 12, wherein said extraction member is integrated with said fixation member.

14. The device according to claim 7, said catheter further including a member extending from said surface to form a mechanical lock for securing said fixation member to said catheter.

15. The device according to claim 14, wherein said extending member includes at least one of a flange, rib, arrow or hook.

16. The method according to claim 8 wherein said fixation member is made of an elastic, open-cell polymer foam.

17. The method according to claim 8, further comprising the step of molding said fixation member with an extraction member for removal of said device following irrigation.

18. The method according to claim 9, wherein the steps set forth for performing the irrigation, including the steps of inserting and removing the catheter, are performed by the person undergoing irrigation and without any need for assistance from another person.

19. The method according to claim 9, wherein the step of removing the catheter is performed without any preliminary compression of said fixation member.

20. The device according to claim 1, wherein the fixation member when expanded has a substantially parabolic shape with a bowl-shaped top surface, relative to a point of catheter insertion, opening in axial alignment with said catheter such that a center area of said top surface is recessed relative to edge areas of said fixation member.

21. The device according to claim 1, wherein the fixation member has an open structure to allow air passing through during irrigation.

22. The device according to claim 1, wherein the fixation member expands without requiring any moisture or fluid flow thereto.

23. The device according to claim 1, wherein the fixation member is fully within said body canal when said catheter is inserted.

24. The device according to claim 2, wherein a base of said expanded fixation member lies closest to an exterior opening of said body canal, said bowl-shaped top surface and sides of said fixation member being pushed downward and outward toward walls of the rectum, respectively, by liquid content therein.

25. The device according to claim 8 wherein the fixation member self-expands without requiring any moisture or fluid flow thereto.

26. The device according to claim 8, wherein said selected position is one that places the fixation member fully within said body canal when said catheter is inserted.

27. The device according to claim 8, wherein said fixation member is molded onto said catheter such that, when expanded, said fixation member has a parabolic shape with a bowl-shaped upper surface opening in axial alignment with said catheter.

28. The device according to claim 9, wherein the step of inserting includes placing the fixation member fully within said body canal such that no portion of said fixation member remains outside said body canal, said fixation member surrounding said catheter but not in fluid communication therewith.

29. The method as set forth in claim 9 wherein during the step of lifting and emptying, said content moves downward onto said bowl-shaped top surface, forcing sides of said fixation member downward and outward toward walls of the rectum to ensure a seal therewith.

30. A device for irrigation of externally debouching, natural or artificial body canals of animals or human beings comprising: a catheter provided on an outer surface thereof with an annular fixation member, said fixation member being made of compressible material in the form of a resilient externally compressed plug-like body of molded material that is self-expandable, said fixation member being compressed by a covering film material that dissolves upon exposure to humidity, said fixation member self-expanding upon dissolution of said covering film material, said catheter including members extending from the surface of the catheter and forming a mechanical lock for the fixation member.

31. A device for irrigation of externally debouching, natural or artificial body canals of animals or human beings comprising: a catheter provided on an outer surface thereof with an annular fixation member, said fixation member being made of compressible material in the form of a resilient compressed plug-like body made of a relatively soft polyurethane foam that is self-expandable, said fixation member being compressed by a covering film material that dissolves upon exposure to humidity, said fixation member self-expanding upon dissolution of said covering film material.

32. A device for irrigation of externally debouching, natural or artificial body canals of animals or human beings comprising: a catheter provided on an outer surface thereof with an annular fixation member, said fixation member being made of compressible material in the form of a resilient compressed plug-like body of molded material that is self-expandable, said fixation member being compressed by a covering film material that dissolves upon exposure to humidity, said fixation member self-expanding upon dissolution of said covering film material and further including an extraction member made of a soft and flexible material with a knitted structure for withdrawal of the device.

33. A device for irrigation of externally debouching, natural or artificial body canals of animals or human beings comprising: a catheter provided on an outer surface thereof with an annular fixation member, said fixation member being made of compressible material in the form of a resilient compressed plug-like body of molded material that is self-expandable, said fixation member being compressed by a covering film material that dissolves upon exposure to humidity, said fixation member self-expanding upon dissolution of said covering film material and further including an extraction member made of a soft and flexible material, including at least one of plastic and fabric, for withdrawal of the device.

* * * * *

UNITED STATES PATENT AND TRADEMARK OFFICE
CERTIFICATE OF CORRECTION

PATENT NO.    : 6,468,245 B2
DATED         : October 22, 2002
INVENTOR(S)   : Alexandersen

It is certified that error appears in the above-identified patent and that said Letters Patent is hereby corrected as shown below:

<u>Title page,</u>
Item [73], the name of the Assignee is corrected as follows:

-- [73]  Assignee: Coloplast A/S, Humlebæk  (DK) --

Signed and Sealed this

Fourth Day of February, 2003

JAMES E. ROGAN
*Director of the United States Patent and Trademark Office*